United States Patent [19]

Deen et al.

[11] 4,277,353

[45] Jul. 7, 1981

[54] OIL-SOLUBLE SUBSTITUTED MONO AND BICYCLIC OXAZOLIDINES, THEIR PREPARATION AND USE AS ADDITIVES FOR FUNCTIONAL FLUIDS

[75] Inventors: Harold E. Deen, Cranford; Rosemary O'Halloran, Union; Esther D. Winans, Colonia; Jack Ryer, East Brunswick, all of N.J.; Stanley J. Brois, Spring, Tex.

[73] Assignee: Exxon Research & Engineering Co., Florham Park, N.J.

[21] Appl. No.: 109,800

[22] Filed: Jan. 7, 1980

[51] Int. Cl.³ ............................................. C10M 1/32
[52] U.S. Cl. ................................ 252/51.5 R; 252/77; 252/392; 548/215; 548/218
[58] Field of Search ..................... 252/77, 51.5 R, 392; 548/215, 218

[56] References Cited

U.S. PATENT DOCUMENTS

| | | | |
|---|---|---|---|
| 2,448,890 | 9/1948 | Johnston | 548/218 |
| 2,564,423 | 8/1951 | Barnum | 548/215 |
| 2,587,955 | 3/1952 | Barnum | 252/392 X |
| 2,752,357 | 6/1956 | Watanabe | 548/215 |
| 3,632,511 | 1/1972 | Liao | 252/51.5 A |
| 3,679,428 | 7/1972 | Shiba et al. | 96/124 |
| 3,738,992 | 6/1973 | Frump | 260/307 F |
| 3,843,726 | 10/1974 | Cobb | 260/570.5 S |
| 4,017,406 | 4/1977 | Brois et al. | 252/51.5 A |
| 4,049,564 | 9/1977 | Ryer et al. | 252/51.5 A |

FOREIGN PATENT DOCUMENTS

| | | |
|---|---|---|
| 564506 | 10/1944 | United Kingdom . |
| 809001 | 2/1959 | United Kingdom . |
| 984409 | 2/1965 | United Kingdom . |

OTHER PUBLICATIONS

Bergmann, Chemical Reviews, 53,309 (1953).
"Chemistry and Use of Aminohydroxy Compounds", Commercial Solvents Corp., New York, N.Y.

*Primary Examiner*—Harris A. Pitlick
*Attorney, Agent, or Firm*—R. A. Dexter; J. J. Mahon

[57] ABSTRACT

Oil-soluble 4-alkyl mono or 5-alkyl bicyclic oxazolidines, e.g. 1-aza-3,7-dioxabicyclo[3.3.0] octanes which are the reaction products of an aldehyde and an amino propane monol or diol are additives which feature activity in functional fluids, e.g. mineral oil base automatic transmission fluids, as copper alloy corrosion inhibitors.

5 Claims, No Drawings

OIL-SOLUBLE SUBSTITUTED MONO AND BICYCLIC OXAZOLIDINES, THEIR PREPARATION AND USE AS ADDITIVES FOR FUNCTIONAL FLUIDS

BACKGROUND OF THE INVENTION

1. Field of the Invention

The invention relates to oil-soluble alkyl substituted mono and bicyclic oxazolidines, e.g. 1-aza-3,7-dioxa-5-ethyl-bicyclo[3.3.0]octane, preferably those substituted in the 2 and/or 8 positions with a group containing at least 3 carbon atoms, which oxazolidines are derived from the reaction of an aldehyde and amino-alkane diol or amino-alkanol.

These oil-soluble adducts have utility as additives for functional fluids, preferably mineral oil compositions, and systems including automatic transmission fluids, lubricating oils and synthetic lubricants.

2. Description of the Prior Art

Lubricant additives derived from a reaction with tris(hydroxymethyl) aminomethane (THAM) are well known and include U.S. Pat. Nos.: 3,756,743; 3,632,511; 3,679,428; and 4,049,564 and United Kingdom Pat. Nos.: 809,001 and 984,409.

In British Pat. No. 564,506, the condensation product of THAM and formaldehyde, i.e. 1-aza-3,7-dioxabicyclo[3.3.0]oct-5-yl methyl alcohols is said to react with fatty acids to give unstable ester products which are useful as drying oils.

U.S. Pat. No. 3,738,992 discusses esters of 1-aza-3,7-dioxabicyclo[3.3.0]oct-5-yl methyl alcohol an antifoam agents and lubricant additives, especially for aqueous textile lubricants.

U.S. Pat. No. 3,843,726 teaches that azadioxabicyclooctane compounds, e.g. 1-aza-5-hydroxymethyl-2,8-diphenyl-3,7-dioxabicyclo[3.3.0]octane (see Example 1), (prepared by reaction of THAM and an aldehyde) can be halogenated to provide an intermediate useful for the preparation of an anti-radiation drug.

Bicyclic oxazolidines are disclosed to be produced from an aldehyde and THAM in a publication entitled Chemistry and use of Aminohydroxy Compounds by Commercial Solvents Corporation, New York, N.Y.

In U.S. Pat. No. 4,017,406 carboxylate esters of aldehyde—THAM adducts are taught to have utility as additives for oleaginous compositions with activity in gasoline as rust inhibitors and carburetor detergents; in automatic transmission fluids as friction modifiers and rust inhibitors; and, in automotive, industrial and lubricating oils as sludge dispersants, rust-inhibitors, friction modifiers and copper alloy corrosion inhibitors, the particular use depending on the molecular weight of the ester.

In prime movers utilizing a functional fluid for power transmission, including hydraulic fluids and automatic transmission fluids, it is generally necessary to remove heat generated during the operation of the functional fluid. One approach involves passing said fluid through a heat exchanger utilizing copper as a structural part or in a brazing mixture joining structural parts, e.g. the automatic transmission fluid of a car is frequently controlled by a heat exchanger located in the car radiator and immersed in the radiator coolant. Operational corrosion of the copper results in mechanically catastrophic intermixing of the functional fluid and radiator coolant (ethylene glycol) and/or loss of said fluid. It is necessary to reduce the copper corrosiveness of said fluid circulating in contact with copper so as to extend the operational lifetime of the prime mover or other mechanical device employing said fluid. One approach is to incorporate a compatible anti-copper corrosion additive into said fluid.

It is an object to this invention to provide an anti-copper-corrosion additive for functional fluids, preferably for automatic transmission fluids.

SUMMARY OF THE INVENTION

It has been discovered that oil-soluble 4-alkyl substituted mono- and 5-alkyl substituted bi-cyclic oxazolidines, e.g. 1-aza-3,7-dioxa-5-ethyl[3.3.0]octane impart excellent anti-copper-corrosion activity to mineral oils and are particularly useful when added in at least a copper-corrosion reducing amount to a functional fluid, preferably a mineral oil system useful as an automatic transmission fluid (ATF) for prime movers.

The oil-soluble additives of the invention can be characterized by the formulas:

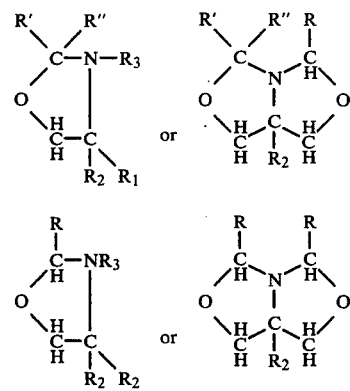

wherein: R is hydrogen or a $C_1$ to $C_{30}$ hydrocarbyl substituent group; R' and R" may be the same or different and each is a $C_1$ to $C_7$ hydrocarbyl substituent group; $R_1$ is hydrogen, methylol, methyl or ethyl; $R_2$ which can be the same as $R_1$ or different is hydrogen, methyl or ethyl; and, $R_3$ is hydrogen or methyl.

The aforesaid additives of the invention are obtained from the reaction of 2 moles of a $C_1$ to $C_{30}$ hydrocarbyl substituted aldehyde or 1 mole of a ketone having 3 to 15 carbons or one mole of said aldehyde and one mole of said ketone per mole of an aminoalkanol (includes both the monool and diol) having from 4 to 7 carbons and preferably according to the formula

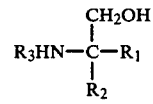

wherein $R_1$, $R_2$ and $R_3$ are the same as earlier defined. Representative compounds illustrative of said formula include: 2-amino-1,3-propanediol; 2-amino-2-methyl-1,3-propanediol; 2-amino-2-ethyl-1,3-propane diol; 2-(methylamino)-1,3-propanediol; and, 2-amino-2-methyl-1-propanol.

Thus according to this invention there is produced a lubricating oil composition comprising a major amount of lubricating oil having dissolved therein at least a copper-corrosion reducing amount of an oil-soluble reaction product of: (a) two moles of a $C_1$ to $C_{30}$ hydrocarbyl substituted aldehyde or (b) one mole of a ketone having from 3 to 15 carbons and then one mole of said aldehyde or (c) one mole of said ketone per mole of an aminoalkanol having from 4 to 7 carbons.

Ketone-Aminoalkanol Adducts

The oil-soluble ketone-aminoalkanol monocyclic oxazolidine adducts, e.g. 2-methyl-2-ethyl-4-methyl-4-methyloloxazolidine-1,3, can be readily prepared by condensing one mole of a ketone with one mole of the aminoalkanol according to the procedures described in the literature by E. D. Bergmann, Chemical Reviews, 53,309 (1953).

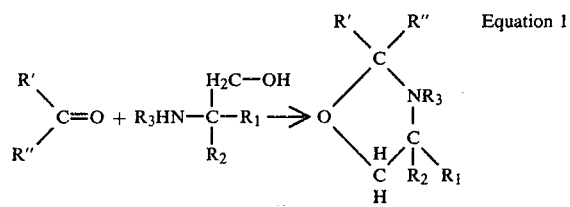

e.g. methyl ethyl ketone+2-amino-2-methyl-1,3-propane diol→2-methyl-2-ethyl-4-methyl-4-methylol-oxazolidine-1,3 whereas the bicyclic oxazolidine adducts can be readily prepared by further condensing the product of Equation 1 (when $R_1$ is methylol and $R_3$ is hydrogen) with an equimolar amount of an aldehyde as depicted in Equation 2.

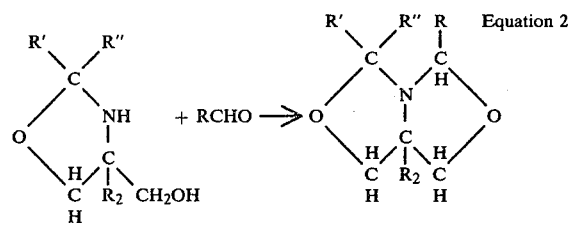

e.g. +formaldehyde→1-aza-2-methyl-2-ethyl-3,7-dioxa-5-methyl-bicyclo[3.3.0]octane.

Aldehyde Aminoalkanol Adducts

The oil-soluble aldehyde-aminoalkanol mono- and bicyclic oxazolidine adducts can be similarly prepared by condensing one or two moles of aldehyde per mole of aminopropane monol or diol, respectively, as presented hereafter in Equations 3 and 4.

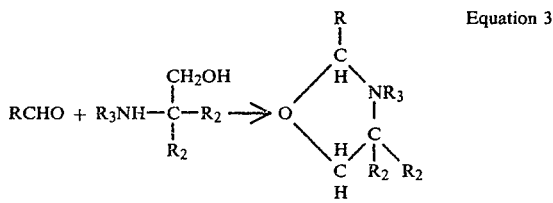

e.g. butyraldehyde+2-amino-2-methyl-1-propanol→2-propyl-4,4-dimethyl-oxazolidine-1,3.

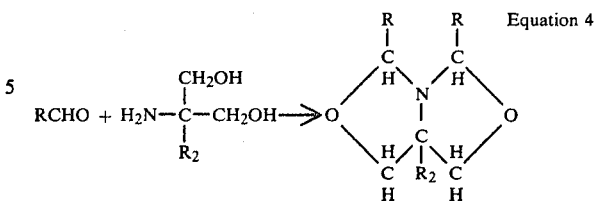

e.g. formaldehyde+2-amino-2-methyl-3-propane diol→1-aza-3,7-dioxa-5-methyl-bicyclo[3.3.0]octane.

The ketone reactants useful in Equation 1 contain from 3 to 15 carbons include acetone, butanone, pentanone, methyl isobutyl ketone, amyl methyl ketone, acetophenone, 2-tridecanone, etc.

The aldehyde reactants have $C_1$ to $C_{30}$ carbons and include formaldehyde, acetaldehyde, propionaldehyde, butyraldehyde, isobutyraldehyde, 2-ethyl-hexanol, dodecyl aldehyde, benzaldhyde, anisaldehyde, naphthaldehyde, phenylacetaldehyde, etc.

The following preparations and examples are included herein as further description and illustrative of the present invention.

EXAMPLE 1

1-aza-3,7-dioxa-5-methyl bicyclo[3.3.0]octane 1.0 mole (105 g) of 2-amino-2 methyl-1,3-propane diol (AMPD) was heated 4 hours with 2.0 moles (60 g) of paraformaldehyde in 200 ml of benzene. 37 ml of water were collected in 4 hours in a Dean Stark trap. The reaction mix was rotoevaporated to remove the benzene and the product was vacuum distilled at 42° C. (0.25 mm. pressure) to give 126 g of distilled product, i.e. 1-aza-3,7-dioxa-5-methyl bicyclo(3.3.0)octane, which analyzed for 55.78% carbon, 7.9% hydrogen and 10.65% nitrogen.

EXAMPLE 2

1-aza-3,7-dioxa-5-ethyl-bicyclo[3.3.0]octane 1.0 mole (119.2 g) of 2-amino-2-ethyl-1,3-propane diol was heated in 200 ml of benzene with 2.0 moles (63 g) of 95% paraformaldehyde. After 3 hours 38 ml of water were collected in a Dean Stark trap. A nitrogen sparge was used to expel the benzene when the water removal was complete. The product, 1-aza-3,7-dioxa-5-ethyl bicyclo[3.3.0]octane, distilled at 37°-38° C. (0.015 mm. pressure) through a Vigreaux column and analyzed for 58.89% carbon, 9.13% hydrogen and 9.56% nitrogen.

EXAMPLE 3

1-aza-3,7-dioxabicyclo[3.3.0]octane 0.3 mole (27.3 g) of 2-amino-1,3-propane diol (APD) was refluxed in 200 ml benzene with 0.63 mole (19.0 g) of paraformaldehyde. The water from the reaction was collected in a Dean Stark trap (12 ml in 1 hour). The benzene was distilled from the reaction mix and the product vacuum distilled at 43°-48° C. at 0.1 mm to 0.2 mm pressure. 33.6 g of distilled product was collected and analyzed for 51.36% carbon, 7.59% hydrogen, and 12.41% nitrogen. This was 1-aza-3,7-dioxabicyclo[3.3.0]octane.

EXAMPLE 4

1-aza-3,7-dioxa-2,8-diisopropyl-5-ethyl bicyclo[3.3.0]octane 1.5 moles (178.8 g) of 2-amino-2-ethyl-1,3-propane diol (AEPD) and 3.0 moles (216 g) isobutrylaldehyde were added to 200 ml of xylene in a 1 liter flask provided with a Dean Stark trap to collect evolved water. The reactants were heated for 5 hours at from 110° to 155° C. After rotoevaporation to remove xylene; on vacuum distillation, the product was obtained as a slightly viscous liquid.

The oil-soluble additives of this invention can be incorporated into a wide variety of functional fluids. They are preferably used in lubricating oil compositions, such as automotive crankcase lubricating oils, automatic transmission fluids, etc., and at concentrations generally within the range of about 0.01 to 1%, preferably 0.05 to 0.5, weight percent of the total composition. Other functional fluids to which the additives can be added include not only mineral oil based fluids, but also fluids based on: lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; and, mixtures of mineral oil and synthetic oil in any proportion, etc.

When the oil-soluble additives of this invention are used as anti-copper-corrosion additives for automatic transmission fluids (ATF), it has been found that these additives do not deteriorate the frictional properties of the ATF i.e. these additives are compatible in ATF. The ATF lubricants contain many other additives which are typically blended into the lubricating mineral oil at the following range of treating levels.

| Components | Concentration range, vol. % |
|---|---|
| V.I. improver | 1–15 |
| Metal Corrosion inhibitor (includes Cu) | 0.01–1 |
| Oxidation inhibitor | 0.01–1 |
| Dispersant | 0.5–10 |
| Pour Point Depressant | 0.01–1 |
| De-emulsifier | 0.001–0.1 |
| Anti-foaming agent | 0.001–0.1 |
| Anti-wear agent | 0.001–1 |
| Seal swellant | 0.1–5 |
| Friction modifier | 0.01–1 |
| Mineral Oil | Balance |

The following data is illustrative of the copper corrosion inhibition improvement of ATF lubricants afforded according to this invention.

The additive product of Example 4 was incorporated into an ATF formulation at a 0.13 wt. % concentration (based on the entire weight of the ATF formulation) as an anti-copper-corrosion inhibitor. The resulting ATF formulation passed the L-2 Friction Test required by the Buick Division of General Motors Corporation and conducted on S.A.E. No. 2 friction apparatus which showed the additive of the invention had no adverse effect on the friction characteristics of the ATF; passed a deemulsibility test; and passed the Turbo Hydromatic Transmission Cycling Test—which is a copper braze corrosion test published in Dexron II Automatic Transmission Fluid Specification by General Motors Co., Detroit, Mich. (see Pub No. 6137-M 2nd Ed. July 1978, Appendix Page 35).

The invention in its broader aspect is not limited to the specific details shown and described and departures may be made from such details without departing from the principles of the invention and without sacrificing its chief advantages.

What is claimed is:

1. A composition comprising a major amount of a functional fluid and a minor but at least a copper-corrosion inhibiting amount of an oil-soluble-4-alkyl mono- or 5-alkyl bicyclic oxazolidine characterized by the formulas:

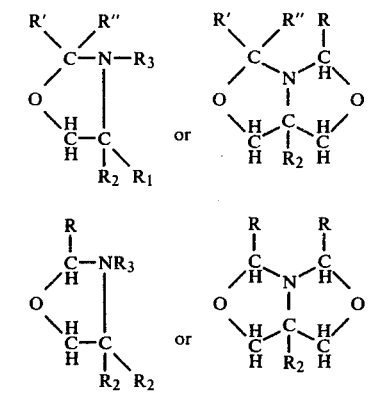

wherein: R is hydrogen or a $C_1$ to $C_{30}$ hydrocarbyl substituent group; R' and R" may be the same or different and each is a $C_1$ to $C_7$ hydrocarbyl substituent group; $R_1$ is hydrogen, methylol, methyl or ethyl; $R_2$ is methyl or ethyl; and $R_3$ is hydrogen or methyl.

2. A composition according to claim 1 wherein said functional fluid is a mineral oil base automatic transmission fluid and said oxazolidine is obtained from the reaction of 1 molar proportion of an amino alkanol having one or two hydroxy groups and 4 to 7 carbons with at least (a) 2 molar proportions of a $C_1$ to $C_{30}$ hydrocarbyl substituted aldehyde or (b) the combination of 1 molar portion of a ketone containing from 3 to 15 carbons and then 1 molar proportion of said aldehyde.

3. A composition according to claim 1 wherein said oxazolidine is 1-aza-3,7-dioxa-2,8-diisopropyl-5-ethylbicyclo[3.3.0]octane present in an amount ranging from 0.01 to 1 weight percent based on the total weight of said compositions and where said functional fluid is a mineral oil base automatic transmission fluid.

4. A composition according to claim 1 wherein said functional fluid is a mineral oil base automatic transmission fluid.

5. A composition according to claim 1 wherein said functional fluid is a mineral lubricating oil.

* * * * *